US006828118B2

(12) United States Patent
Xu (10) Patent No.: US 6,828,118 B2
(45) Date of Patent: Dec. 7, 2004

(54) REVERSE-PHASE HPLC ASSAY FOR PLASMINOGEN ACTIVATORS

(75) Inventor: Yuan Xu, Redwood City, CA (US)

(73) Assignee: Genentech, Inc., South San Francisco, CA (US)

(*) Notice: Subject to any disclaimer, the term of this patent is extended or adjusted under 35 U.S.C. 154(b) by 20 days.

(21) Appl. No.: 10/443,701

(22) Filed: May 21, 2003

(65) Prior Publication Data

US 2003/0199016 A1 Oct. 23, 2003

Related U.S. Application Data

(63) Continuation of application No. 09/703,695, filed on Nov. 1, 2000, now Pat. No. 6,593,097.
(60) Provisional application No. 60/163,607, filed on Nov. 4, 1999.

(51) Int. Cl.$^7$ ................................................ C12Q 1/37
(52) U.S. Cl. ........................................................ 435/23
(58) Field of Search .................... 435/23, 7.4; 530/300, 530/350

(56) References Cited

U.S. PATENT DOCUMENTS

| | | |
|---|---|---|
| 4,766,075 A | 8/1988 | Goeddel et al. |
| 4,777,043 A | 10/1988 | Bennett et al. |
| 5,120,535 A | 6/1992 | Marquardt et al. |
| 5,409,700 A | 4/1995 | Heim et al. |
| 5,411,864 A | 5/1995 | Anicetti et al. |
| 5,612,029 A | 3/1997 | Bennett et al. |
| 5,753,486 A | 5/1998 | Goeddel et al. |
| 5,753,702 A | 5/1998 | Bednar et al. |

FOREIGN PATENT DOCUMENTS

WO     WO 89/04367     5/1989

OTHER PUBLICATIONS

Anicetti and Hancock., "Analytical Considerations in the Development of Protein Purification Processes." *Bioprocess. Technol.* 18:11–36 (1994).
Apffel et al., "Application of capillary electrophoresis, high–performance liquid chromatography, on–line electrospray mass spectometry and matrix–assisted laser desorption ionization–time of flight mass spectometry to the characterization of single–chain plasminogen activator" *J Chrom A* 717:41–60.
Apffel et al., "Application of New Analytical Technology to the Production of a "Well–Characterized Biological"." *Dev. Biol. Stand.* 96:11–25 (1998).
Astrup and Fermin, "Fibrinolysis in the Animal Organism" *Nature* 159:681–682 (1947).
Benedict et al., "New variant of human tissue plasminogen activator (TPA) with enhanced efficacy and lower incidence of bleeding compared with recombinant human TPA" *Circulation* 92 (10):3032–3040 (1995).

Camiolo et al., "Fabrinogenolysis and fibrinolysis with tissue plasminogen activator, urokinase, streptokinase–activated human globulin, and plasmin" *Proc. Soc. Exp. Biol. Med.* 138:277–280 (1971).
Carr et al., "Selective identification and differentiation of N– and O–linked oligosaccharides in glycoproteins by liquid chromatography–mass spectrometry" *Protein Science* 2:183–196 (1993).
Collen et al., "Molecular mechanism of fibrinolysis and their application to fibrin–specific thrombolytic therapy" *Journal of Cellular Biochemistry* 33 (2):77–86 (1987).
Conboy and Henion, "The Determination of Glycopeptides by Liquid Chromatography/Mass Spectrometry with Collision–Induced Dissociation" *J. Am. Soc. Mass Spectrom.* 3:804–814 (1992).
de Vos et al., "Crystal Structure of the Kringle 2 Domain of Tissue Plasminogen Activator at 2.4–A Resolution" *Biochemistry* 31:270–279 (1992).
Guzzetta et al., "Identification of Carbohydrate Structures in Glycoprotein Peptide Maps by the Use of LC/MS with Selected Ion Extraction with Special Reference to Tissue Plasminogen Activator and a Glycosylation Variant Produced by Site Directed Mutagenesis" *Anal. Chem.* 65:2953–2962 (1993).
Hoylaerts et al., "Kinetics of the Activation of Plasminogen by Human Tissue Plasminogen Activator" *Journal of Biological Chemistry* 257:2912–2919 (1982).
Huddleston et al., "Collisional Fragmentation of Glycopeptides by Electrospray Ionization LC/MS and LC/MS/MS: Methods for Selective Detection of Glycoepeptides in Protein Digests" *Anal. Chem.* 65: 877–884 (1993).
Ichinose et al., "Proteolytic activation of tissue plasminogen activator by plasma and tissue enzymes" *FEBS Letters* 175:412–418 (1984).
Keyt et al., "A Faster–Acting and More Potent Form of Tissue Plasminogen Activator." *Proc. Natl. Acad. Sci. USA* 91:3670–3674 (1994).
Kwiatkowski et al., "Effects of tissue plasminogen activator for acute ischemic stroke at one year" *New Eng. J. Med.* 340(23):1781–1787 (1999).

(List continued on next page.)

*Primary Examiner*—Karen Cochrane Carlson
*Assistant Examiner*—Sheridan Snedden
(74) *Attorney, Agent, or Firm*—Janet E. Hasak (57) ABSTRACT

A process is described for monitoring the effectiveness of a purification process in removing plasminogen activator (PA) endogenous to Chinese hamster ovary (CHO) cells from a sample containing human tPA or variants thereof. This process comprises incubating the sample with a protease capable of specifically cleaving the $Arg_{275}$-$Ile_{276}$ bond of human wild-type tPA and then with denaturing/reducing agents in respective amounts effective to reduce the disulfide bonds of human wild-type tPA; subjecting the sample to a reversed-phase high-performance liquid chromatography step, and analyzing the elution profile from the chromatography step for the amount of PA endogenous to the CHO cells present therein.

6 Claims, 3 Drawing Sheets

OTHER PUBLICATIONS

Ling et al., "Characterization of the Tryptic Map of Recombinant DNA Derived Tissue Plasminogen Activator by High–Performance Liquid Chromatography–Electropray Ionization Mass Spectrometry" *Anal. Chem.* 63:2909–2915 (1991).

Modi et al., "Pharmacokinetics of a Slower Clearing Tissue Plasminogen Activator Variant, TNK–tPA, in Patients with Acute Myocardial Infarction" *Thrombosis and Haemostasis* 79:134–139 (1998).

Nguyen and Ward, "Stability Characterization and Formulation Development of Altepase, a Recombinant Tissue Plasminogen Activator" *Stability and Characterization of Protein and Peptide Drugs: Case Histories*, Wang and Pearlman, New York:Plenum Press pps. 91–135 (1993).

Pennica et al., "Cloning and Expression of Human Tissue–type Plasminogen Activator cDNA in *E. coli*," *Nature* 301:214–221 (1983).

Rijken and Collen, "Purification and Characterization of the Plasminogen Activator Secreted by Human Melanoma Cells in Culture," *Journal of Biological Chemistry* 256(13):7035–7041 (1981).

Smith et al., "Emergency Physician Treatment of Acute Stroke with Recombinant Tissue Plasminogen Activator: A Retrospective Analysis" *Acad. Emergency Medicine* 6(6):618–625 (1999).

Thomas et al., "A Long–Half–life and Fibrin–Specific Form of Tissue Plasminogen Activator in Rabbit Models of Embolic Stroke and Peripheral Bleeding" *Stroke* 25:2072–2079 (1994).

Wiebe and May, "Cell Banking" *Large Scale Mammalian Cell Culture Technology*, Lubiniecki, New York:Marcel Dekker pps. 147–160 (1990).

SEQUENCE LISTING

<160> NUMBER OF SEQ ID NOS: 4
<210> SEQ ID NO 1
<211> LENGTH: 4
<212> TYPE: PRT
<213> ORGANISM: Artificial Sequence
<220> FEATURE:
<223> OTHER INFORMATION: Partial sequence.

<400> SEQUENCE: 1

Lys His Arg Arg
 1

<210> SEQ ID NO 2
<211> LENGTH: 4
<212> TYPE: PRT
<213> ORGANISM: Artificial Sequence
<220> FEATURE:
<223> OTHER INFORMATION: Partial Sequence.

<400> SEQUENCE: 2

Ala Ala Ala Ala
 1

<210> SEQ ID NO 3
<211> LENGTH: 2544
<212> TYPE: DNA
<213> ORGANISM: Homo sapiens

<400> SEQUENCE: 3

| | | | | |
|---|---|---|---|---|
| gttctgagca | cagggctgga | gagaaaacct | ctgcgaggaa | agggaaggag | 50 |
| caagccgtga | atttaaggga | cgctgtgaag | caatcatgga | tgcaatgaag | 100 |
| agagggctct | gctgtgtgct | gctgctgtgt | ggagcagtct | tcgtttcgcc | 150 |
| cagccaggaa | atccatgccc | gattcagaag | aggagccaga | tcttaccaag | 200 |
| tgatctgcag | agatgaaaaa | acgcagatga | tataccagca | acatcagtca | 250 |
| tggctgcgcc | ctgtgctcag | aagcaaccgg | gtggaatatt | gctggtgcaa | 300 |
| cagtggcagg | gcacagtgcc | actcagtgcc | tgtcaaaagt | tgcagcgagc | 350 |
| caaggtgttt | caacggggc | acctgccagc | aggccctgta | cttctcagat | 400 |
| ttcgtgtgcc | agtgccccga | aggatttgct | gggaagtgct | gtgaaataga | 450 |
| taccagggcc | acgtgctacg | aggaccaggg | catcagctac | aggggcacgt | 500 |
| ggagcacagc | ggagagtggc | gccgagtgca | ccaactggaa | cagcagcgcg | 550 |
| ttggcccaga | agcctacag | cgggcggagg | ccagacgcca | tcaggctggg | 600 |
| cctggggaac | cacaactact | gcagaaaccc | agatcgagac | tcaaagccct | 650 |
| ggtgctacgt | ctttaaggcg | gggaagtaca | gctcagagtt | ctgcagcacc | 700 |
| cctgcctgct | ctgagggaaa | cagtgactgc | tactttggga | atgggtcagc | 750 |
| ctaccgtggc | acgcacagcc | tcaccgagtc | gggtgcctcc | tgcctcccgt | 800 |
| ggaattccat | gatcctgata | ggcaaggttt | acacagcaca | gaaccccagt | 850 |
| gcccaggcac | tgggcctggg | caaacataat | tactgccgga | atcctgatgg | 900 |
| ggatgccaag | ccctggtgcc | acgtgctgaa | gaaccgcagg | ctgacgtggg | 950 |
| agtactgtga | tgtgccctcc | tgctccacct | gcggcctgag | acagtacagc | 1000 |
| cagcctcagt | ttcgcatcaa | aggagggctc | ttcgccgaca | tcgcctccca | 1050 |

```
                                                                        -continued ccccctggcag gctgccatct ttgccaagca caggaggtcg cccggagagc                      1100
ggttcctgtg cgggggcata ctcatcagct cctgctggat tctctctgcc                      1150
gcccactgct tccaggagag gtttccgccc caccacctga cggtgatctt                      1200
gggcagaaca taccgggtgg tccctggcga ggaggagcag aaatttgaag                      1250
tcgaaaaata cattgtccat aaggaattcg atgatgacac ttacgacaat                      1300
gacattgcgc tgctgcagct gaaatcggat tcgtcccgct gtgcccagga                      1350
gagcagcgtg gtccgcactg tgtgccttcc cccggcggac ctgcagctgc                      1400
cggactggac ggagtgtgag ctctccggct acggcaagca tgaggccttg                      1450 tctccttttct attcggagcg gctgaaggag gctcatgtca gactgtaccc                     1500
atccagccgc tgcacatcac aacatttact aacagaaca gtcaccgaca                       1550 acatgctgtg tgctggagac actcggagcg gcgggcccca ggcaaacttg                      1600
cacgacgcct gccagggcga ttcgggaggc cccctggtgt gtctgaacga                      1650
tggccgcatg actttggtgg gcatcatcag ctggggcctg gctgtggac                       1700 agaaggatgt cccgggtgtg tacaccaagg ttaccaacta cctagactgg                      1750
attcgtgaca acatgcgacc gtgaccagga acacccgact cctcaaaagc                      1800
aaatgagatc ccgcctcttc ttcttcagaa gacactgcaa aggcgcagtg                      1850
cttctctaca gacttctcca gacccaccac accgcagaag cgggacgaga                      1900
ccctacagga gagggaagag tgcatttttcc cagatacttc ccattttgga                     1950
agttttcagg acttggtctg atttcaggat actctgtcag atgggaagac                      2000
atgaatgcac actagcctct ccaggaatgc ctcctccctg ggcagaaagt                      2050
ggccatgcca ccctgttttc agctaaagcc caacctcctg acctgtcacc                      2100
gtgagcagct ttggaaacag gaccacaaaa atgaaagcat gtctcaatag                      2150
taaaagataa caagatcttt caggaaagac ggattgcatt agaaatagac                      2200
agtatattta tagtcacaag agcccagcag ggcctcaaag ttggggcagg                      2250
ctggctggcc cgtcatgttc ctcaaaagca cccttgacgt caagtctcct                      2300 tccccttttcc ccactccctg gctctcagaa ggtattcctt ttgtgtacag                     2350
tgtgtaaagt gtaaatcctt tttctttata aactttagag tagcatgaga                      2400
gaattgtatc atttgaacaa ctaggcttca gcatatttat agcaatccat                      2450
gttagttttt actttctgtt gccacaaccc tgttttatac tgtacttaat                      2500
aaattcagat atatttttca cagttttttcc aaaaaaaaaa aaaa                           2544
```

<210> SEQ ID NO 4
<211> LENGTH: 562
<212> TYPE: PRT
<213> ORGANISM: Homo sapiens

<400> SEQUENCE: 4

```
Met Asp Ala Met Lys Arg Gly Leu Cys Cys Val Leu Leu Leu Cys
  1               5                  10                  15

Gly Ala Val Phe Val Ser Pro Ser Gln Glu Ile His Ala Arg Phe
                 20                  25                  30

Arg Arg Gly Ala Arg Ser Tyr Gln Val Ile Cys Arg Asp Glu Lys
                 35                  40                  45

Thr Gln Met Ile Tyr Gln Gln His Gln Ser Trp Leu Arg Pro Val
                 50                  55                  60
```

```
Leu Arg Ser Asn Arg Val Glu Tyr Cys Trp Cys Asn Ser Gly Arg
                65                  70                  75

Ala Gln Cys His Ser Val Pro Val Lys Ser Cys Ser Glu Pro Arg
                80                  85                  90

Cys Phe Asn Gly Gly Thr Cys Gln Gln Ala Leu Tyr Phe Ser Asp
                95                 100                 105

Phe Val Cys Gln Cys Pro Glu Gly Phe Ala Gly Lys Cys Cys Glu
               110                 115                 120

Ile Asp Thr Arg Ala Thr Cys Tyr Glu Asp Gln Gly Ile Ser Tyr
               125                 130                 135

Arg Gly Thr Trp Ser Thr Ala Glu Ser Gly Ala Glu Cys Thr Asn
               140                 145                 150

Trp Asn Ser Ser Ala Leu Ala Gln Lys Pro Tyr Ser Gly Arg Arg
               155                 160                 165

Pro Asp Ala Ile Arg Leu Gly Leu Gly Asn His Asn Tyr Cys Arg
               170                 175                 180

Asn Pro Asp Arg Asp Ser Lys Pro Trp Cys Tyr Val Phe Lys Ala
               185                 190                 195

Gly Lys Tyr Ser Ser Glu Phe Cys Ser Thr Pro Ala Cys Ser Glu
               200                 205                 210

Gly Asn Ser Asp Cys Tyr Phe Gly Asn Gly Ser Ala Tyr Arg Gly
               215                 220                 225

Thr His Ser Leu Thr Glu Ser Gly Ala Ser Cys Leu Pro Trp Asn
               230                 235                 240

Ser Met Ile Leu Ile Gly Lys Val Tyr Thr Ala Gln Asn Pro Ser
               245                 250                 255

Ala Gln Ala Leu Gly Leu Gly Lys His Asn Tyr Cys Arg Asn Pro
               260                 265                 270

Asp Gly Asp Ala Lys Pro Trp Cys His Val Leu Lys Asn Arg Arg
               275                 280                 285

Leu Thr Trp Glu Tyr Cys Asp Val Pro Ser Cys Ser Thr Cys Gly
               290                 295                 300

Leu Arg Gln Tyr Ser Gln Pro Gln Phe Arg Ile Lys Gly Gly Leu
               305                 310                 315

Phe Ala Asp Ile Ala Ser His Pro Trp Gln Ala Ala Ile Phe Ala
               320                 325                 330

Lys His Arg Arg Ser Pro Gly Glu Arg Phe Leu Cys Gly Gly Ile
               335                 340                 345

Leu Ile Ser Ser Cys Trp Ile Leu Ser Ala Ala His Cys Phe Gln
               350                 355                 360

Glu Arg Phe Pro Pro His His Leu Thr Val Ile Leu Gly Arg Thr
               365                 370                 375

Tyr Arg Val Val Pro Gly Glu Glu Gln Lys Phe Glu Val Glu
               380                 385                 390

Lys Tyr Ile Val His Lys Glu Phe Asp Asp Thr Tyr Asp Asn
               395                 400                 405

Asp Ile Ala Leu Leu Gln Leu Lys Ser Asp Ser Ser Arg Cys Ala
               410                 415                 420

Gln Glu Ser Ser Val Val Arg Thr Val Cys Leu Pro Pro Ala Asp
               425                 430                 435

Leu Gln Leu Pro Asp Trp Thr Glu Cys Glu Leu Ser Gly Tyr Gly
               440                 445                 450
```

```
Lys His Glu Ala Leu Ser Pro Phe Tyr Ser Glu Arg Leu Lys Glu
            455                 460                 465

Ala His Val Arg Leu Tyr Pro Ser Ser Arg Cys Thr Ser Gln His
            470                 475                 480

Leu Leu Asn Arg Thr Val Thr Asp Asn Met Leu Cys Ala Gly Asp
            485                 490                 495

Thr Arg Ser Gly Gly Pro Gln Ala Asn Leu His Asp Ala Cys Gln
            500                 505                 510

Gly Asp Ser Gly Gly Pro Leu Val Cys Leu Asn Asp Gly Arg Met
            515                 520                 525

Thr Leu Val Gly Ile Ile Ser Trp Gly Leu Gly Cys Gly Gln Lys
            530                 535                 540

Asp Val Pro Gly Val Tyr Thr Lys Val Thr Asn Tyr Leu Asp Trp
            545                 550                 555

Ile Arg Asp Asn Met Arg Pro
            560
```

REVERSE-PHASE HPLC ASSAY FOR PLASMINOGEN ACTIVATORS

RELATED APPLICATIONS

This is a continuation application filed under 37 CFR 1.53(b) of application Ser. No. 09/703,695, filed Nov. 1, 2000, now U.S. Pat. No. 6,593,097 which is non-provisional application filed under 37 CFR 1.53(b)(1), claiming priority under 35 USC 119(e) to provisional application No. 60/163,607 filed Nov. 4, 1999, the entire contents of which are incorporated herein by reference.

BACKGROUND OF THE INVENTION

1. Field of the Invention

This invention is directed to an assay for determining the amount of Chinese Hamster Ovary (CHO)-produced tPA present in samples of recombinant human tPA with native sequence or its variants produced in CHO cells.

2. Description of Related Art

Tissue-type plasminogen activators (tPA) are endogenous serine proteases involved in a cascade of events leading to the dissolution of a blood clot (Astrup and Permin, *Nature*, 159, 681–682 (1947); Camiolo et al., *Proc. Soc. Exp. Biol. Med.*, 138, 277–280 (1971); Collen, *J. Cell. Biochem.*, 33, 77–86 (1987); Hoylaerts et al., *J. Biol. Chem.*, 257, 2912–2919 (1982)). ACTIVASE® is the recombinant form of human tPA (r-tPA), used in the management of acute myocardial infarction and pulmonary embolism (Grossbard, *Pharm. Res.*, 4, 375–378 (1987)). ACTIVASE® is also now approved for treating ischemic stroke (Smith et al., *Acad. Emergency Medicine*, 6(6), 618–25 (1999); Kwiatkowski et al., *New Eng. J. Med.*, 340(23), 1781–1787 (1999)). It is a glycoprotein produced by expressing the complementary DNA (cDNA) for natural human tPA in CHO cells. TNK-tPA is a genetically engineered variant of human tPA cloned and expressed in CHO cells (Keyt et al., *Proc. Natl. Acad. Sci USA.*, 91, 3670–3674 (1994)). Site-directed mutations were introduced at three specific sites of human tPA to create the TNK-tPA variant. They are Thr103 to Asn (T103N), Asn 117 to Gln (N117Q), and Lys-His-Arg-Arg (SEQ ID NO:1) 296–299 to Ala-Ala-Ala-Ala (SEQ ID NO:2) (KHRR296–299AAAA). When compared to tPA, TNK-tPA exhibits similar in vitro biological activity, an increased resistance to plasminogen activator inhibitor and an enhanced fibrin specificity, and is cleared more slowly from plasma (Keyt et al., *Proc. Natl. Acad. Sci USA.*, 91, 3670–3674 (1994); Thomas et al., *Stroke*, 25:10, 2072–2079 (1994); Benedict et al., *Circulation*, 92:10, 3032–3040 (1995); Modi et al., *Thromb Haemost*, 79, 134–139 (1998)). It is currently awaiting regulatory approval as a single bolus administered form of r-tPA. CHO cells biosynthesize endogenous hamster tPA called CHO-PA. CHO-PA has a similar fibrinolytic activity to human tPA as determined by the clot lysis assay. The amino acid sequence of CHO-PA is 80% identical to that of human tPA. Many of the substitutions are semi-conservative such as: Arg<--->Lys, Glu<--->Asp, Phe<--->Tyr, Val<--->Ala, Ile<--->Leu, or Thr<--->Ser. Using a model of the human tPA protease domain based upon the bovine chymotrypsin structure, it is observed that virtually all of the substitutions in CHO-PA are localized at or near the protein surface.

r-tPA, TNK-tPA, and CHO-PA are all single polypeptide chains composed of 527 amino acids with 17 disulfide bonds (Nguyen and Ward, "Stability Characterization and Formulation Development of Altepase, a Recombinant Tissue Plasminogen Activator," in *Stability and Characterization of Protein and Peptide Drugs: Case Histories*, Y. J. Wang, R. Pearlman, eds., (Plenum Press: New York, 1993), pp. 91–135). For all three proteins, the peptide bond between $Arg_{275}$ and $Ile_{276}$ is particularly susceptible to protease cleavage. The cleavage results in two fragments: one consisting of the N-terminal 275 amino acids and the other consisting of the C-terminal 252 amino acids. The N-terminal chain contains regions which are homologous to the kringle regions found in plasminogen and prothrombin and, therefore, is often referred to as the "kringle fragment" (Nguyen and Ward, supra; de Vos et al., *Biochem.*, 31, 270–279 (1992)).

The C-terminal chain contains the catalytically active site and, therefore, is commonly referred to as the "protease fragment" (Pennica et al., *Nature*, 301, 214–221 (1983)). The cleaved two chains are linked by a single disulfide bond formed between $Cys_{264}$ and $Cys_{395}$. The cleaved molecule is commonly referred to as "two-chain tPA" as opposed to "single-chain tPA" or the intact form.

r-tPA contains four potential sites for N-linked glycosylation identified by the sequence Asn-X-Ser/Thr (Nguyen and Ward, supra). These are $Asn_{117}$, $Asn_{184}$, $Asn_{218}$, and $Asn_{448}$. r-tPA exists as two glycosylation isozymes designated type I and type II. Type I r-tPA is glycosylated at $Asn_{117}$, $Asn_{184}$, and $Asn_{448}$; whereas type II r-tPA is glycosylated only at $Asn_{117}$ and $Asn_{448}$. $Asn_{218}$ is not glycosylated in either isoform. TNK-tPA has the same glycosylation pattern as r-tPA, except that the Thr103 to Asn and Asn117 to Gln mutations effectively moved the glycosylation site from position 117 to 103 (Keyt et al., supra). The glycosylation pattern for CHO-PA is not fully characterized (Rijken and Collen, *J. Biol. Chem.*, 256: 7035–7041 (1981)).

ACTIVASE® is a trademark for the recombinant form of human tissue-type plasminogen activator (r-tPA), used in the management of acute myocardial infarction and pulmonary embolism. ACTIVASE® brand tPA is also now approved for treating ischemic stroke. It is produced by expressing the complementary DNA (cDNA) for natural human tPA in CHO cells (U.S. Pat. No. 5,753,486). TNK-tPA is a genetically engineered variant of r-tPA with enhanced efficacy and lower incidence of bleeding compared with ACTIVASE® r-tPA. It was created by three site-directed mutations (T103N, N117Q and KHRR (SEQ ID NO:1) 296–299AAAA (SEQ ID NO:2)), and is also cloned and expressed in CHO cells (U.S. Pat. No. 5,612,029). CHO cells biosynthesize endogenous hamster tPA called CHO-PA. The amino acid sequence of CHO-PA is highly homologous (80% identical) to that of r-tPA. All three thrombolytic proteins exist as heterogeneous isoforms, mainly due to proteolysis/hydrolysis and differential glycosylation.

A method for purifying human tPA from CHO-PA is described in U.S. Pat. No. 5,411,864. This method-comprises contacting a fluid containing the human tPA with antibodies specifically binding the corresponding endogenous CHO-PA and recovering the human tPA. Preferably the contacting step involves passing the fluid through a chromatographic bed having the antibodies immobilized thereon.

The development of recombinant DNA-derived protein pharmaceuticals has been facilitated by the introduction of new analytical methods that can be used to characterize protein and/or to demonstrate consistency of manufacture of a protein. Peptide mapping is a key method for monitoring the amino acid sequence and is able to detect small changes in small-to moderate-size proteins, for example, insulin and human growth hormone. The analysis of a much larger protein, e.g., fibrinogen (molecular mass of 350,000), or the heterogeneous glycoproteins, such as antibodies (molecular mass of 150,000), is hindered by the complexity of the range of peptides generated by an enzymatic digestion. Such complexity makes a single reversed-phase high-performance liquid chromatography (RP-HPLC) separation combined with on-line ultraviolet detection of limited utility.

The advent of commercially available combined HPLC and electrospray ionization mass spectromety (LC-ES-MS) systems compatible with convention HPLC has increased the power of peptide mapping considerably (Ling et al., *Anal. Chem.*, 63: 2909–2915 (1991); Guzzetta et al., *Anal. Chem.*, 65: 2953–2962 (1993)). LC-EM-MS in combination with in-source collisionally induced dissociation (CID) has been used effectively to identify sites of N-and O-linked glycosylation (Carr et al., *Protein Sci.*, 2: 183–196 (1993); Huddleston et al., *Anal. Chem.*, 65: 877–884 (1993); Conboy and Henion, *J. Am. Soc. Mass Spectrom.*, 3: 804–814 (1992)).

However, even this technique is limited by insufficient resolution resulting from the large number of very similar peptides caused by variable protein glycosylation and enzymatic digests of moderately sized glycoproteins. It is therefore necessary to employ a range of techniques with orthogonal selectivity to characterize such samples.

The use of combinations of high-performance capillary electrophoresis, HPLC, LC-ES-MS, and matrix-assisted laser desorption ionization-time of flight mass spectrometry has been investigated to allow for characterization of enzymatic digests of underivatized glycoprotein samples, as exemplified by DSPAα1, a single-chain plasminogen activator derived from vampire bat salivary glands (Apffel et al., *J. Chromatography A*, 717: 41–60 (1995)). It was concluded that these four techniques are highly complimentary techniques for examining glycoproteins. Nonetheless, the authors acknowledge that more work needs to be done to improve the power of this approach, and that high-yield concentration steps will be required due to extensive carbohydrate heterogeneity.

There is a need for a technique to monitor the relative and absolute amounts of CHO-PA present after a purification procedure for tPA is carried out, such as the one reported in U.S. Pat. No. 5,411,864, supra.

SUMMARY OF THE INVENTION

Accordingly, a reversed-phase HPLC method was developed herein for the analysis of the three thrombolytic molecules, CHO-tPA, recombinant human tPA with native sequence, and TNK-tPA. This method not only has the ability to resolve human tPA and/or TNK-tPA from CHO-PA, but also is capable of identifying and quantifying different isoforms of each molecule.

Specifically, the present invention provides a process for monitoring the effectiveness of a purification process in removing plasminogen activator (PA) endogenous to Chinese hamster ovary (CHO) cells from a sample containing human tPA or variants thereof, which process comprises incubating the sample with a protease capable of specifically cleaving the $Arg_{275}$-$Ile_{276}$ bond of human wild-type tPA and then with denaturing and reducing agents in amounts effective to reduce the disulfide bonds of human wild-type tPA; subjecting the sample to a reversed-phase high-performance liquid chromatography step, and analyzing the elution profile from the chromatography step for the amount of PA endogenous to the CHO cells present therein.

DESCRIPTION OF THE PREFERRED EMBODIMENTS

Definitions

The terms "tissue plasminogen activator" and "tPA" refer to human extrinsic (tissue-type) plasminogen activator having fibrinolytic activity that typically has a structure with five domains (finger, growth factor, kringle-1, kringle-2, and protease domains), but nonetheless may have fewer domains or may have some of its domains repeated if it still functions as a thrombolytic agent and retains the N-linked glycosylation sites at positions 117, 184, and 448. At minimum, the tPA consists of a protease domain that is capable of converting plasminogen to plasmin, and an N-terminal region believed to be at least partially responsible for fibrin binding, and retains the N-linked glycosylation sites at positions corresponding to amino acid positions 117, 184, and 448 of wild-type human tPA. The retention of these glycosylation sites is due to the fact that variable-site occupancy of recombinant and melanoma-derived wild-type tPA leads to production of two variants, designated as "Type I tPA" and "Type II tPA", respectively. Type I tPA contains N-linked oligosaccharides at positions 117, 184, and 448. Type II tPA contained N-linked oligosaccharides at positions 117 and 448. It will be understood that natural allelic variations exist and can occur among individuals, as demonstrated by one or more amino acid differences in the amino acid sequence of tPA of each individual.

The terms "wild-type human tissue plasminogen activator", "wild-type human tPA", "native human tissue plasminogen activator," and "native human tPA", where "human tPA" may be abbreviated as "htPA", refer to native-sequence human tPA, i.e., that encoded by the cDNA sequence reported in U.S. Pat. No. 4,766,075, issued Aug. 23 1988, which cDNA sequence is disclosed therein as (SEQ ID NO:3)
5'-GTTCTGAGCACAGGGCTGGAGAGAAAACCTCTGCGAGCAAAGGGAAGGAGCAAGCCGTGAATTTAAGGGACGC

TGTGAAGCAATC ATG GAT GCA ATG AAG AGA GGG CTC TGC TGT GTG CTG CTG GTG TGT GGA

GCA GTC TTC GTT TCG CCC AGC CAG GAA ATC CAT GCC CGA TTC AGA AGA GGA GCC AGA

-continued

```
TCT TAC CAA GTG ATC TGC AGA GAT GAA AAA ACG CAG ATG ATA TAC CAG CAA CAT CAG
TCA TGG CTG CGC CCT GTG CTC AGA AGC AAC CGG GTG GAA TAT GCT GGG TGC AAC AGT
GGC AGG GCA CAG TGC CAC TCA GTG CCT GTC AAA AGT TGC AGe GAG CCA AGG TGT TTC
AAC GGG GGC ACC TGC CAG CAG GCC CTG TAC TTC TCA GAT TTC GTG TCC AGT GCC CCC
GAA GGA TTT GCT GGG AAG TGC TGT GAA AlA CAT ACC AGG GCC ACG TGC TAC GAG GAC
CAG GGC ATC AGC TAC AGG GGC ACG TGG AGC ACA GCG GAG AGT GGC GCC GAG TGC ACC
AAC TGG AAC AGC AGC CCC TTC GCC CAG AAG CCC TAC AGC GGG CGG AGG CCA GAC GCC
ATC ACC CTG CCC CTG GGG AAC CAC AAC TAC TCC AGA AAC CCA GAT CGA GAC TCA AAC
CCC TGG TGC TAC GTC TTT AAG GCG GGG AAG TAC AGC TCA GAG TTC TGC AGC ACC CCT
GCC TGC TCT GAG CCA AAC ACT CAC TCC TAC TTT GGG AAT GGG TCA GCC TAC CGT GGC
ACG CAC AGC CTC ACC GAG TCG GGT GCC TCC TGC CTC CGG TGG AAT TCC ATG ATC CTG
ATA GGC AAC GTT TAC ACA GCA CAG AAC CCC AGT GCC CAG GCA GTC GGC CTG GGC AAA
CAT AAT TAC TGC CGG AAT CCT GAT GGG GAT GCC AAG CCC TGG TGC CAC CTG CTG AAG
AAC CGC AGG CTG ACG TGG GAG TAC TGT GAT GTG CCC TCC TGC TCC ACC TGC GGC CTG
AGA CAG TAC AGC CAG CCT CAG TTT CGC ATC AAA GGA GGG CTC TTC GCC GAC ATC GCC
TCC CAC CCC TGG CAG GCT CCC ATC TTT GCC AAG CAC AGG AGC TCG CCC GGA GAG CGG
TTC CTG TGC GGG GGC ATA CTC ATC AGC TCC TGC TGG ATT CTC TCT GCC GCC CAC TGC
TTC CAG GAG AGG TTT CCG CCC CAC CAC CTG ACG GTG ATC TTG GGC AGA ACA TAC CGG
GTG GTC CCT GGC GAG GAG GAG CAG AAA TTT GAA GTC GAA AAA TAC ATT GTC CAT AAG
GAA TTC GAT GAT GAC ACT TAC GAC AAT GAC ATT GCG CTG CTG CAG CTG AAA TCG GAT
TCG TCC CGC TGT GCC CAG GAG AGC AGC GTG GTC GCA CAC TGT GCA CTT CCC CCG GCG
GAC CTG CAG CTG CCG GAC TGG ACG GAG TGT GAG CTC TCC GGC TAC GGC AAG CAT GAG
GCC TTG TCT CCT TTC TAT CGA GAG CGG CTG AAG GAG GGT CAT GTC AGA CTG TAG CCA
TCC AGC CGC TGC ACA TCA CAA CAT TTA CTT AAC AGA ACA GTC ACC GAC AAC ATG CTG
TGT GCT GGA GAC ACT CGG AGC GGC GGG CCC CAG GCA AAC TTG CAC GAC GCC TGC AGG
GGC GAT TCG GGA GGC CCC CTG GTG TGT CTG AAC GAT GGC CGC ATG ACT TTG GTG GGC
ATC ATC AGC TGG GGC CTG GGC TGT GGA CAG AAG GAT GTC CCG GGT GTG TAC ACC AAG
GTT ACC AAC TAC CTA GAC TGG ATT CGT GAC AAC ATG CGA CCG TGA
CCAGGAACACCCGACTCCTCAAAAGCAAATGAGATCCCGCCTCTT
CTTCTTCAGAAGACACTGCAAAGGCGCAGTGCTTCTCTACAGACTTCTCCAGACCCACCACACCGCAGAAGCGGG
ACGAGACCCTACAGGAGAGGGAAGAGTGCATTTTCCCAGATACTTCCCATTTTGGAAGTTTTCAGGACTTGG
TCTGATTTCAGGATACTCTGTCAGATGGGAAGACATGAATGCACACTAGCCTCTCCAGGAATGCCTCCTCCCTGGG
CAGAAAGTGGCCATGCCACCCTGTTTTCAGCTAAAGCCCAACCTCCTGACCTGTCACCGTGAGCAGCTTTGGAAAC
AGGACCACAAAAATGAAAGCATGTCTCAATAGTAAAAGATAACAAGATCTTTCAGGAAAGACGGATTGCATTAGAA
ATAGACAGTATATTTATAGTCACAAGAGCCCAGCAGGGCCTCAAAGTTGGGGCAGGCTGGCTGGCCCGTCATGTTC
CTCAAAAGCACCCTTGACGTCAAGTCTCCTTCCCCTTTCCCCACTCCCTGGCTCTCAGAAGGTATTCCTTTTGTGT
ACAGTGTGTAAAGTGTAAATCCTTTTTCTTTATAAACTTTAGAGTAGCATGAGAGAATTGTATCATTTGAACAACT
AGGCTTCAGCATATTTATAGCAATCCATGTTAGTTTTTACTTTCTGTTGCCACAACCCTGTTTTATACTGTACTTA
ATAAATTCAGATATATTTTTCACAGTTTTTCCAAAAAAAAAAAAAA-3'.
```

Amino acid site numbers or positions in the tPA molecule are labeled in accordance with U.S. Pat. No. 4,766,075, the numbered amino acid sequence -continued being disclosed therein as:

(SEQ ID NO:4)

met asp ala met lys arg gly leu cys cys val leu leu cys gly ala val phe val ser pro ser gln glu ile his ala arg phe arg arg gly ala arg SER TYR

GLN VAL ILE CYS ARG ASP GLU LYS THR GLN MET ILE TYR GLN GLN HIS GLN SER TRP LEU

ARG PRO VAL LEG ARG SEE ASN ARG VAL GLU TYR CYS TRP CYS ASN SER GLY ARG ALA GLN

CYS HIS SER VAL PRO VAL LYS SER CYS SER GLU PRO ARG CYS PHE ASN GLY GLY THR CYS

GLN GLN ALA LEU TYR PHE SER ASP PHE VAL CYS GLN CYS PRO GLU GLY PHE ALA GLY LYS

CYS CYS GLU ILE ASP THR ARG ALA THR CYS TYR GLU ASP GLN GLY ILE SER TYR ARG GLY

THR TRP SER THR ALA GLU SER GLY ALA GLU CYS THR ASN TRP ASN SER SER ALA LEU ALA

GLN LYS PRO TYR SER GLY ARG ARG PRO ASP ALA ILE ARG LEU GLY LEU GLY ASN HIS ASN

TYR CYS ARG ASN PRO ASP ARG ASP SER LYS PRO TRP CYS TYR VAL PHE LYS ALA GLY LYS

TYR SER SER GLU PHE CYS SER THR PRO ALA CYS SER GLU GLY ASN SER ASP CYS TYR PHE

GLY ASN GLY SER ALA TYR ARG GLY THR HIS SER LEU THR GLU SER GLY ALA SER CYS LEU

PRO TRP ASN SER MET ILE LEU ILE GLY LYS VAL TYR THR ALA GLN ASN PRO SER ALA GLN

ALA LEU GLY LEU GLY LYS HIS ASN TYR CYS ARG ASN PRO ASP GLY ASP ALA LYS PRO TRP

CYS HIS VAL LEU LYS ASN ARG ARG LEU THR TRP GLU TYR CYS ASP VAL PRO SER CYS SER

THR CYS GLY LEU ARG GLN TYR SER GLN PRO GLN PHE ARG ILE LYS GLY GLY LEU PHE ALA

ASP ILE ALA SER HIS PRO TRP GLN ALA ALA ILE PHE ALA LYS HIS ARG ARG SER PRO GLY

GLU ARG PHE LEU CYS GLY GLY ILE LEU ILE SER SER CYS TRP ILE LEU SER ALA ALA HIS

CYS PHE GLN GLU ARG PHE PRO PRO HIS HIS LEU THR VAL ILE LEU GLY ARG THR TYR ARG

VAL VAL PRO GLY GLU GLU GLU GLN LYS PHE GLU VAL GLU LYS TYR ILE VAL HIS LYS GLU

PHE ASP ASP ASP THR TYR ASP ASN ASP ILE ALA LEU LEU GLN LEU LYS SER ASP SER SER

ARG CYS ALA GLN GLU SER SER VAL VAL ARG THR VAL CYS LEU PRO PRO ALA ASP LEU GLN

LEU PRO ASP TRP THR GLU CYS GLU LEU SER GLY TYR GLY LYS HIS GLU ALA LEU SER PRO

PHE TYR SER GLU ARG LEU LYS GLU ALA HIS VAL ARG LEU TYR PRO SER SER ARG CYS THR

SER GLN HIS LEU LEU ASN ARG THR VAL THR ASP ASN MET LEU CYS ALA GLY ASP THR ARG

SER GLY GLY PRO GLN ALA ASN LEU HIS ASP ALA CYS GLN GLY ASP SER GLY GLY PRO LEU

VAL CYS LEU ASN ASP GLY ARG MET THR LEU VAL GLY ILE ILE SER TRP GLY LEU GLY CYS

GLY GLN LYS ASP VAL PRO GLY VAL TYR THR LYS VAL THR ASN TYR LEU ASP TRP ILE ARG

ASP ASN MET ARG PRO OP.

As used herein, references to various domains of tPA mean the domains of wild-type human tPA as hereinabove defined, and functionally equivalent portions of human tPA having amino acid alterations as compared to the native human tPA sequence, or of (native or variant) tPA from other sources, such as bat tissue plasminogen activator (bat-PA). Thus, as used herein, the term "protease domain" refers to the region extending from amino acid position 264 to amino acid position 527, inclusive, of the mature form of wild-type human tPA, and to functionally equivalent portions of human tPA having amino acid alterations as compared to the native human tPA sequence, or of tPA from other sources, such as bat-PA.

As used herein, "tPA variants" refers to molecules that differ from native tPA by one or more amino acid changes or modifications to existing amino acids. TNK-tPA is the preferred variant herein. The modification to change or insert the appropriate amino acid(s) in the native molecule to effect the desired sequence variations is accomplished by any means known in the art, such as e.g. site-directed mutagenesis or ligation of the appropriate sequence into the DNA encoding the relevant protein.

As used herein, "TNK-tPA" refers to a tPA molecule wherein Thr103 of wild-type tPA is changed to Asn (T103N), Asn117 of wild-type tPA is changed to Gln (N117Q), and Lys-His-Arg-Arg (SEQ ID NO:1) 296–299 of wild-type tPA is changed to Ala-Ala-Ala-Ala (SEQ ID NO:2) (KHRR296–299AAAA). Such TNK is further described in U.S. Pat. No. 5,612,029.

The term "Chinese hamster ovary cell" or "CHO cell" refers to cells or cell lines derived from Chinese hamster ovaries, as described, for example, in EP 117,159, published Aug. 29, 1989; U.S. Pat. Nos. 4,766,075; 4,853,330; 5,185, 259; and Lubiniecki et al., in Advances in Animal Cell Biology and Technology for Bioprocesses, Spier et al., eds. (1989), pp. 442–451), as well as CHO derivatives such as CHO/-DHFR (Urlaub and Chasin, *Proc. Natl. Acad. Sci. USA*, 77: 4216 (1980)), CHO-K1 DUX B11 (Simonsen and Levinson, *Proc. Natl. Acad. Sci. USA*, 80: 2495–2499 (1983); Urlaub and Chasin, supra), and dp12.CHO cells (EP 307,247 published Mar. 15 1989) Preferred host cells include CHO-K1 DUX B11 and dp12.CHO cells.

The CHO cells developed for large-scale production of tPA are maintained cryogenically in a MCB/working cell bank (WCB) system as described by Wiebe et al., in *Large Scale Mammalian Cell Culture Technology*, Lubiniecki, ed., (Marcel Dekker: New York, 1990), pp. 147–160. DHFR+ CHO-K1 cells transfected with DNA encoding human tPA have been deposited at the American Type Culture Collection, Manassas, Va. (ATCC), and are available under accession number CCL 61. A sample of another tPA-producing CHO cell line (CHO cell line 1–15$_{15}$) has been deposited under ATCC accession number CRL 9606. The latter cell line was reported to result in human tPA levels approaching 50 pg/cell/day.

As used herein, "CHO plasminogen activator" or "CHO-PA" refers to plasminogen activator that is produced endogenously by CHO cells. This endogenous PA expressed by CHO cells has a sequence slightly different (about 80% identical) from the human wild-type tPA. The CHO-PA is not a tissue-type PA.

As used herein, "protease" refers to an enzyme that is capable of cleaving the Arg$_{275}$-Ile$_{276}$ bond of human wild-type tPA specifically. Examples include plasmin (or plasminogen, which converts to plasmin), tissue kallikrein, or Factor Xa, as well as any trypsin-like proteases that can effect this specific, limited proteolysis. Eligible proteases are further described in Ichinose et al., *FEBS Letters*, 175: 412–418 (1984). Preferred herein is plasmin/plasminogen.

As used herein, "denaturing/reducing agents" or "denaturing agent and reducing agent" refers to a combination of denaturant and reductant that reduces the disulfide bonds of human wild-type tPA. Preferably, the denaturing agent is guanidine or urea and the reducing agent is dithiothreitol (DTT) or 2-mercaptoethanol.

Modes for Carrying Out the Invention

After recombinant production, the tPA or tPA variant is recovered from the CHO culture medium, either as a secreted protein or from host cell lysates when directly expressed without a secretory signal. It is necessary to purify the tPA or variant thereof from host cell proteins to obtain preparations that are substantially homogeneous as to protein. As a first step, the culture medium or lysate is centrifuged or filtered to remove particulate cell debris.

The human tPA or variant thereof is then purified from corresponding contaminant endogenous proteins such as CHO-PA by such techniques as fractionation on immunoaffinity or ion-exchange columns as described, for example, in U.S. Pat. No. 5,411,864; ethanol precipitation; reverse phase HPLC; chromatography on silica or on a cation exchange resin such as DEAE; chromatofocusing; SDS-PAGE; ammonium sulfate precipitation; or gel electrophoresis using, for example, SEPHADEX™ G-75 medium. A protease inhibitor that does not interfere with the tPA activity such as phenylmethylsulfonyl fluoride (PMSF) also may be useful to inhibit proteolytic degradation during purification, and antibiotics may be included to prevent the growth of adventitious contaminants. One skilled in the art will appreciate that purification methods suitable for native tPA may require modification to account for changes in the character of tPA or its variants upon expression in recombinant cell culture.

In a preferred embodiment, if a tPA variant is being produced, it is secreted and the supernatant is passed over a phosphate-buffered saline (PBS)-preconditioned column of glass beads coupled to anti-tPA goat polyclonal A6 antibody, the column is equil-ibrated with a buffer, and the tPA variant is then eluted.

The invention herein is directed to monitoring (including qualifying and quantifying) levels of native CHO-PA in a sample taken from such purification systems that contains at least one form of human tPA that is produced in CHO cells. The process comprises incubating the sample with a protease that is capable of cleaving the Arg$_{275}$-Ile$_{276}$ bond specifically. This is followed by incubation of the protease-treated sample with a combination of a denaturing and reducing agent in proper relative and absolute amounts to effect reduction of the disulfide bonds in human wild-type tPA. Since the treatment with denaturing and reducing agents causes the loss of enzyme activity, the incubation with protease occurs first.

After incubation, the sample is subjected to a reversed-phase high-performance liquid chromatography step, and the elution profile from the chromatography step analyzed for the amount of PA endogenous to the CHO cells present therein. Preferably, the protease is plasminogen, which converts to the active form, plasmin, the human tPA is native-sequence tPA, and the tPA variant is TNK-tPA.

The consecutive incubation step with the protease followed by the denaturing/reducing agents typically takes place at a temperature of about 30–40° C., more preferably about 36–38° C., and most preferably about 37° C., for a minimum of about 15 minutes, more preferably about 20–40 minutes.

Also, preferably before incubation, the sample is diluted with a digestion buffer, which preferably has a pH of about 7 to 8, more preferably phosphate buffer at pH 7.4–7.6, and more preferably also containing arginine.

Any suitable HPLC column on which the sample is loaded may be utilized for the purposes of this invention, including preparative or analytical scale. The column is typically equilibrated for at least about 15 minutes prior to sample injection. Column size, column material, flow rate, elution buffers, type of gradient, injection volume, and particle size of column depend on various factors, including the size of the sample being examined, the type of mobile phase composition and gradient, and the forms of tPA being distinguished.

The loading solvent may be any solvent but is preferably an acetonitrile-based solvent such as water, acetonitrile, and trifluoroacetic acid (TFA). Preferably, the column is a ZORBAX™ C8, VYDAC™, or BAKER™ C-18 column packed with a medium having a particle diameter of about 4–40 *m, more preferably about 5–15 *m, and a pore size of about 100–4000 *, more preferably about 150–350 *. Also, the medium preferably has a C4, C8, or C18 alkyl group, and most preferably is a C8 silica medium. Preferably, the elution is carried out with a solvent comprising acetonitrile, such as water, acetonitrile, and TFA, in a gradient format over 60–100 minutes, preferably a linear gradient, wherein the relative amount of acetonitrile is increased in the solvent. In another preferred embodiment, a shallow gradient ramp at about 0.25% acetonitrile per minute is employed If the analysis for purity herein indicates that the technique employed successfully removes CHO-PA, further purification steps can be carried out as necessary to remove any other contaminants. If the technique did not successfully remove CHO-PA to acceptable levels, a different purification scheme can be utilized and the process herein repeated to determine how effective that scheme is.

After final purification, the tPA or variant thereof can be formulated according to known methods to prepare pharmaceutically useful compositions, whereby the tPA product is combined in admixture with a pharmaceutically acceptable carrier. Such formulations are well described in the literature as well as dosages and uses. For example, the tPA or its variant is suitably administered parenterally to subjects suffering from cardiovascular diseases or conditions and strokes.

The following examples are intended to illustrate one embodiment now known for practicing the invention, but the invention is not to be considered limited to these examples. All open and patented literature citations herein are expressly incorporated by reference.

EXAMPLE 1

Materials

ACTIVASE® (r-tPA) and TNK-tPA were obtained from Genentech, Inc. (South San Francisco, Calif.) in a form purified from CHO cells. See also, for example, U.S. Pat. Nos. 4,766,075 and 5,753,486 for ACTIVASE® r-tPA and U.S. Pat. No. 5,612,029 for TNK-tPA.

Monoclonal antibody #354 for CHO-PA was produced as described in U.S. Pat. No. 5,411,864. Briefly, a female Balb/c mouse was immunized over a period of 12 weeks with protein solutions substantially enriched in CHO plasminogen activator purified from host cells lacking the human t-PA. There were five injections each consisting of approximately 30 μg. The initial injection was emulsified with complete Freund's adjuvant and administered in subcutaneous site(s). The second injection given 1.5 weeks later was emulsified with incomplete Freund's adjuvant and half was administered subcutaneously and half intraperitoneally. The remaining three injections were given on weeks 3, 6 and 12 in phosphate buffered saline (PBS) administered in one intraperitoneal site.

The spleen from the immunized mouse was removed on week 13 and spleen cells were fused with the mouse myeloma cell line NP3X63-Ag8.653 using the general procedures of Fazekas et al., *J. Immunol. Methods*, 35: 1 (1980) and Lane, *J. Immunol. Methods* 81: 223 (1985). The fused cells were distributed into ten microtiter plates each containing 96 wells. Each well was screened for specific antibody production using differential reactivity in two ELISA's (enzyme-linked immunoadsorbant assays). One ELISA specifically detected antibodies against CHO-PA and the second detected antibodies that cross-reacted with recombinant human tPA.

Approximately 5% of the total wells were reactive only with CHO-PA, and 3% reacted with CHO-PA and human t-PA.

Hybridoma cells from wells containing CHO-PA-specific antibodies were expanded and cloned by limiting dilution (Oi and Herzenberg, "Immunoglobin-Producing Hybrid Cell Lines", p. 351–372, in *Selected Methods in Cellular Immunology*, Mishell and Shiigi, eds. (W. H. Freeman and Co., 1980)). Large quantities of specific monoclonal antibodies were produced by cell culture of the hybridoma cells or by injection of hybridoma cells in mice, thereby producing ascites tumors MAb 354 was one resulting antibody, which lowered CHO-PA levels greater than about 100 fold in a single column pass when immobilized and is stable to several different immobilization chemistries and harsh washing conditions.

MAb 354 was purified using the steps set forth below, where all steps were carried out at room temperature. Concentration was carried out as follows: The MAb hybridoma suspension culture harvest fluid (HF) was filtered through a 0.2 μm filter. The culture fluid was concentrated by ultrafiltration or by chromatography on an ion-exchange resin.

Affinity purification was carried out as follows: Thimerosal was added to the concentrated MAb HF solution to approximately 0.02%. The solution was adjusted to approximately 1.5 M glycine, 3.0 M NaCl, pH 9.0, by addition of 3.0 M glycine, followed by addition of crystalline NaCl. Protein A has poor Ab binding, so addition of NaCl and glycine increases hydrophobic interaction, so as to facilitate Ab binding. The solution was clarified by filtration. The clarified concentrated MAb HF was applied to a column of protein A immobilized to agarose. The bound MAb was washed with the buffer used to equilibrate the column, having the approximate composition of 1.5 M glycine, 3.0 M NaCl, 0.02 M EDTA, pH 9.0. The MAb was eluted with 0.1 M sodium citrate, 0.15 M NaCl, pH 3.0 buffer. The protein A column was regenerated by washing with 3.0 M NaSCN, 0.03 M TRIS, pH 8.5, and re-equilibrated. The eluted MAb peak was collected based on absorbance profile at 280 nm. The citrate-eluted MAb peak was immediately neutralized by collection into buffer with the approximate composition: 1.5 M TRIS-HCl, pH 9.0. After use, the protein A column was unpacked and stored in sealed containers at 2–8° C. in approximately 0.02% thimerosal as storage buffer.

The 354 MAb was then buffer exchanged by diafiltration. Diafiltration proceeded until the conductivity and pH were similar to the values for 0.03 M TRIS, 0.05 M NaCl, pH 8.5 buffer.

The MAb was subsequently applied to an anion-exchange chromatography column containing DEAE-FAST FLOW™ agarose support and washed with 0.03 M TRIS, 0.05 M NaCl, pH 8.5 buffer. The MAb was step eluted with a buffer having the approximate composition: 0.03 M TRIS, 0.15 M NaCl, pH 8.5. The eluted MAb peak was collected based on absorbance profile at 280 nm.

The MAb was filtered (0.2 μm) into sanitized sealable containers and stored below –40° C.

Plasminogen was obtained from Fluka (Switzerland). HPLC-grade acetonitrile was obtained from Burdick & Jackson (Muskgon, Mich.) and trifluoroacetic acid (TFA) was from Pierce (Rockford, Ill.). Water for the HPLC mobile phase and sample solutions was purified with a MILLI-Q™ system from Millipore (Milford, Mass.). All other chemicals were of reagent grade from Sigma (St. Louis, Mo.).

Methods

Purification of CHO-PA

CHO-PA was isolated from CHO cell culture fluid by affinity chromatography followed by immunoabsorption. Lysine HYPER™ D resin from BioSepra (Paris, France) was used for the affinity chromatography, as lysine binds to the kringle 2 region of plasminogen activators (Cleary et al., *Biochem.* 28, 1884–1890 (1989)). The immunoabsorption was conducted by using CHO-PA specific monoclonal antibody #354 (MAb#354). MAb#354 was coupled to CNBr-activated SEPHAROSE 4B™ gel according to the vendor's protocol (Pharmacia Biotech, Piscataway, N.J.). About 10 mg of MAb #354 was coupled to the CNBr-activated SEPHAROSE 4B™ gel. After coupling, a MAb#354-SEPHAROSE 4B™ column was packed.

CHO cell culture fluid containing secreted CHO-PA was loaded onto a lysine-affinity column pre-equilibrated with an equilibration buffer containing 50 mM sodium phosphate and 0.01% POLYSORBATE 80™ detergent at pH 7.5. After loading, the lysine-affinity column was washed three times: first with the equilibration buffer, followed by a buffer containing 40 mM TRIS, 800 mM NaCl, and 0.008%

POLYSORBATE 80™ at pH 8.0, and finally with the equilibration buffer. CHO-PA was then eluted from the lysine affinity column with a buffer containing 50 mM sodium phosphate, 200 mM L-arginine, and 0.01% POLYSORBATE 80™ at pH 7.5. After equilibrating with phosphate-buffered saline (PBS, 8 g/L NaCl, 0.2 g/L KCl, 1.44 g/L $Na_2HPO_4$ and 0.24 g/L $KH_2PO_4$ at pH 7.4), the MAb#354-SEPHAROSE™ 4B column was loaded with the lysine-affinity column elution pool. After loading, the column was washed with a buffer containing 9.5 mM $Na_2HPO_4$, 1 M NaCl, and 5% propylene glycol (v/v) at pH 7.4. The bound CHO-PA was eluted from the column with 0.2 M glycine-HCl at pH 2.5. The elution was monitored spectrophotometrically at 280 nm and the CHO-PA-containing fractions were neutralized with 0.14 volumes of 1.5 M arginine-phosphate (pH 8.0) immediately upon collection. The identity and purity of the eluted CHO-PA was confirmed by SDS-PAGE and amino acid sequence analysis.

DTT/Urea Treatment

The solution containing plasminogen activator(s) was diluted 1:1 (v/v) with a denaturation buffer (8 M urea, 0.5 M TRIS, and 3.2 mM EDTA at pH 8.4). Dithiothreitol (DTT) was added from a 1-M stock solution to a final concentration of 20 mM, and the mixture was incubated at 37° C. for 30 min.

Plasmin Treatment

The solution containing plasminogen activator(s) was diluted 1:3 (v/v) with the digestion buffer (125 mM $Na_2HPO_4$, 200 mM arginine, and 0.01% $NaN_3$ at pH 7.5). One hundredth (w/w) of plasminogen was added, and the mixture was incubated at 37° C. for 30 min.

Reversed-Phase HPLC Assay for Plasminogen Activators

The assay was performed on a HEWLETT-PACKARD 1090M™ HPLC system (Hewlett Packard, Avondale, Pa.) with a 4.6-mm×250-mm, 5-μm particle size, 300 Å pore resin, ZORBAX SB-C8™ column (Mac-Mod, Chadds Ford, Pa.). The column was equilibrated for at least 15 minutes prior to sample injection. The initial mobile phase composition was 70/30/0.1 (v/v/v) of water/acetonitrile/TFA. After a five-minute initial hold, a linear gradient was performed in 80 minutes (for FIGS. 1 and 2) and in 60 minutes (for FIG. 3) to 50/50/0.1 (v/v/v) of water/acetonitrile/TFA. Immediately following the gradient, the column was regenerated for 10 minutes with 100/0.1 (v/v) of acetonitrile/TFA. The composition was then brought back to the initial conditions in 5 minutes, and the system was re-equilibrated for the next injection. The injection volume was 250 mL, and the flow rate was 1 mL/min. The chromatography was conducted at 40° C. Fluorescence was measured with a HEWLETT-PACKARD 1046A™ programmable fluorescence detector (Ex=275 nm and Em=340 nm). The chromatograms were recorded and analyzed with Hewlett-Packard CHEMSTATION™ software.

Results and Discussion

Due to high sequence homology, ACTIVASE® (r-tPA), TNK-tPA, and CHO-PA have very similar biochemical/biophysical properties. Analytical and preparative methods capable of resolving these three plasminogen activators from each other or capable of resolving tPA from CHO-PA or TNK-tPA from CHO-PA are needed for recovery process development and to estimate the purity of each molecule for clinical studies and commercial production. Described herein is a simple reverse-phase HPLC method that accomplishes these goals.

Figure 1:
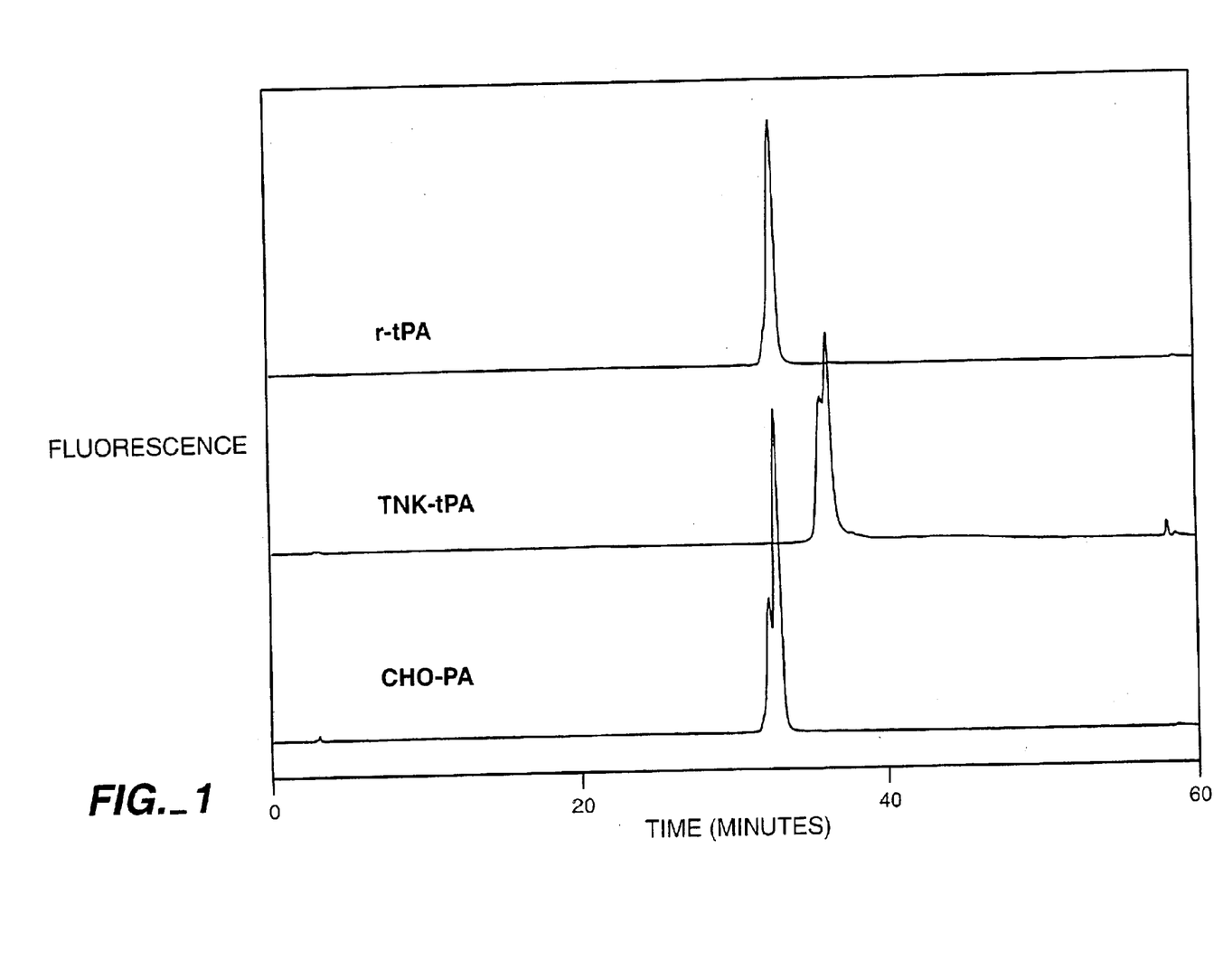
FIG. 1 shows a reversed-phase HPLC analysis of native r-tPA, TNK-tPA and CHO-PA.

With a shallow gradient ramp at 0.25% acetonitrile per minute and no protease or denaturing/reducing agents, reversed-phase HPLC was not able to separate the native form of r-tPA from native CHO-PA (FIG. 1). However, the native form of TNK-tPA was resolved very well from both native r-tPA and CHO-PA under these conditions. Next, DTT/urea treatment was performed to reduce the disulfide bonds and denature the proteins. For all three proteins, the peptide bond between $Arg_{275}$ and $Ile_{276}$ is very susceptible to protease cleavage. Over time, this susceptibility leads to heterogeneity for r-tPA, TNK-tPA, and CHO-PA in solution. A small amount of the single-chain form is converted to the two-chain form due to the protease cleavage. DTT/urea treatment reduces the disulfide bond between $Cys_{264}$ and $Cys_{395}$ that holds the two-chain form of the molecule together, resulting in the dissociation of the molecule into two fragments (the kringle fragment and the protease fragment).

Figure 2:
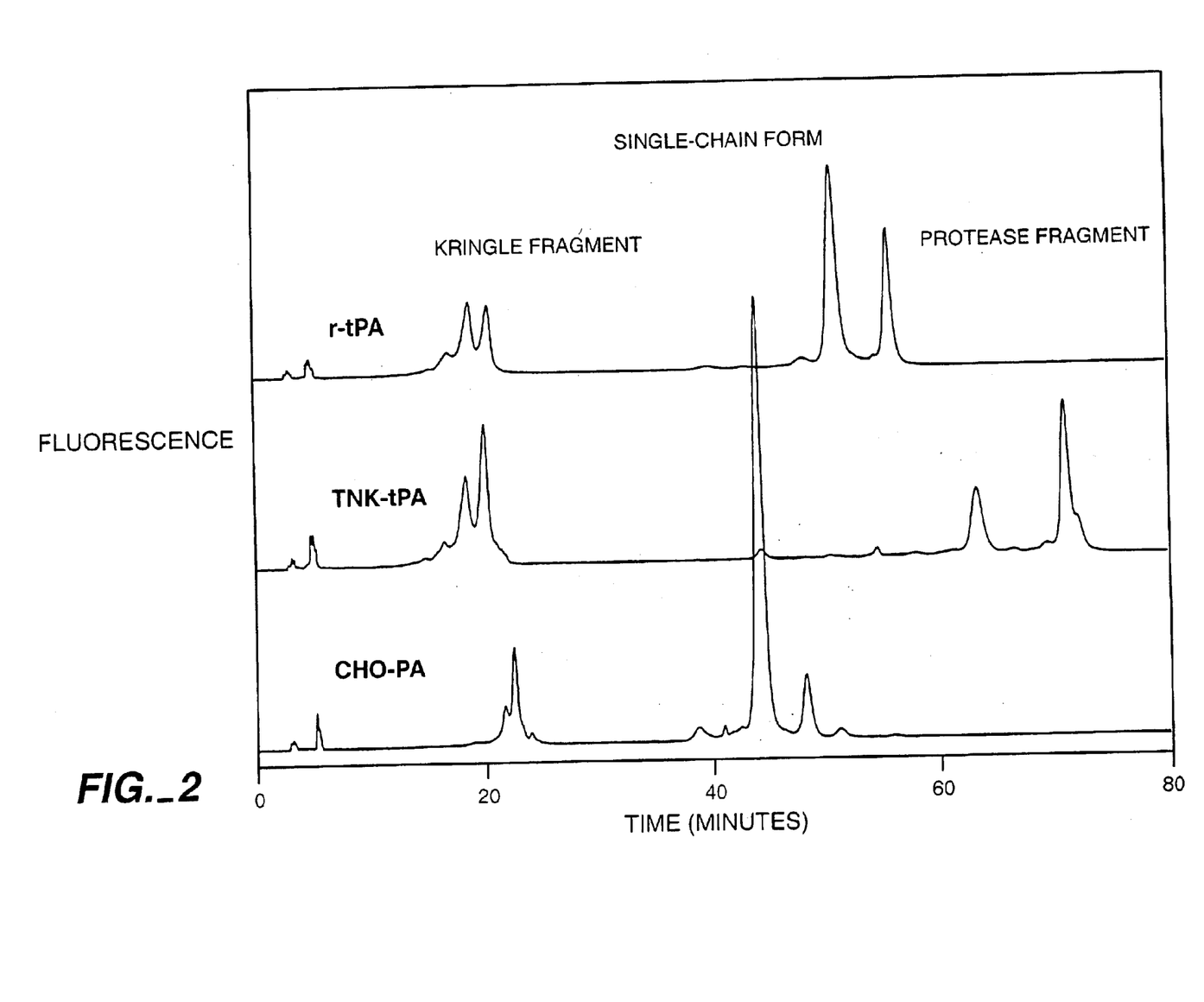
FIG. 2 shows a reversed-phase HPLC analysis of DTT/urea-treated r-tPA, TNK-tPA and CHO-PA. Plasminogen activators were treated with DTT/urea prior to chromatography.

FIG. 2 shows that, under the same gradient ramp, reversed-phase HPLC was able to resolve the single-chain form of the three thrombolytic molecules from each other after DTT/urea treatment. All three proteins exhibited similar elution profiles with the kringle fragment of the two-chain form eluting first, the single-chain form eluting second, and the protease fragment of the two-chain form eluting last. The respective protease fragments of the three plasminogen activators were also well resolved from each other, while the kringle fragments for the three molecules were not well separated. Consequently, this method can be used to detect and quantify the fragmentation of the single-chain form into the two-chain form of the plasminogen activators.

The heterogeneity observed in the r-tPA, TNK-tPA, and CHO-PA profiles (FIG. 2) makes the quantification of these molecules very difficult, especially when trying to quantify each individual molecule in a mixture of rtPA, TNK-tPA, and CHO-PA. To eliminate the heterogeneity associated with proteolysis, all of the single-chain form was converted to two-chain form by incubating with plasminogen. Plasminogen is the substrate of plasminogen activator in the natural fibrinolytic system. r-tPA, TNK-tPA, and CHO-PA all have the enzymatic activity of cleaving the $Arg_{560}$—$Val_{561}$ peptide bond of plasminogen. Such cleavage converts plasminogen into its active form, plasmin. Plasmin is a serine protease with low specificity and is capable of cleaving the $Arg_{275}$—$Ile_{276}$ peptide bond in r-tPA, TNK-tPA, and CHO-PA. As a result, incubation with plasminogen converts the single-chain form of the three plasminogen activators to the two-chain form.

Figure 3:
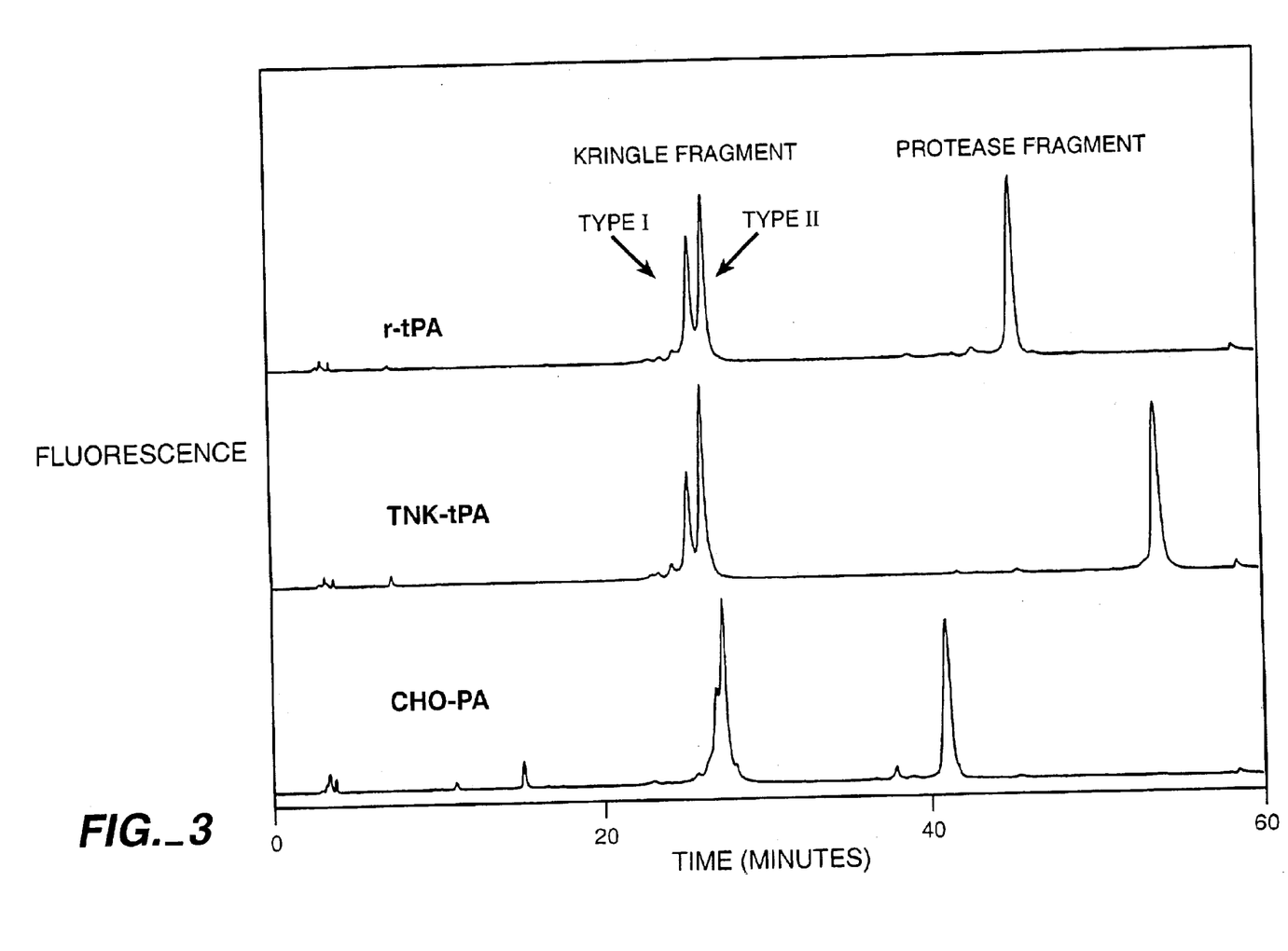
FIG. 3 shows a reversed-phase HPLC analysis of plasmin-and DTT/urea-treated r-tPA, TNK-tPA and CHO-PA. Plasminogen activators were subjected to plasmin treatment followed by DTT/urea treatment prior to chromatography.

Following the plasmin treatment, the samples were treated with DTT/urea to reduce disulfide bonds and thus dissociate the two-chain form of the molecule into two discrete fragments. FIG. 3 shows the reversed-phase HPLC profiles for the plasmin-and DTT/urea-treated plasminogen activators. The respective protease fragments of the three proteins were well separated from each other, while the kringle fragments of the three molecules were not resolved. Therefore, the protease fragment was used for the integration and quantification of each plasminogen activator. For both r-tPA and TNK-tPA, the kringle fragments from the type I and type II isozymes were well separated. As a result, this method is also useful for the quantification of the type I to type II ratio for both r-tPA and TNK-tPA.

The availability of this reversed-phase HPLC method greatly facilitates the manufacturing process development. It has been used to evaluate the effect of different fermentation conditions on product quality regarding the integrity of the product (i.e. single chain percent) and the ratio of type I and type II isozymes. It has also been used to aid the purification process development and to ensure consistency between production batches. All those applications exemplify the crucial role of analytical and commercial methods in the development of new pharmaceutics.

What is claimed is:

1. A process for quantifying the ratio of type I to type II isozymes of human wild-type tPA (SEQ ID NO:4) or a variant or variants thereof in a sample comprising same, which process comprises:
   (a) incubating the sample with a protease capable of specifically cleaving the $\text{Arg}_{275}$-$\text{Ile}_{276}$ bond of said human wild-type tPA;
   (b) incubating the sample from step (a) with a denaturing agent and a reducing agent in amounts effective to reduce the disulfide bonds of said human wild-type tPA;
   (c) subjecting the sample to a reversed-phase high-performance liquid chromatography step; and
   (d) analyzing the elution profile from the chromatography step for the relative amounts of type I and type II isozymes present.

2. The process of claim 1 wherein the protease is plasminogen.

3. The process of claim 1 wherein the sample comprises human wild-type tPA (SEQ ID NO:4).

4. The process of claim 1 wherein the tPA variant is a tPA molecule wherein Thr103 of human wild-type tPA (SEQ ID NO:4) is changed to Asn, Asn117 of human wild-type tPA (SEQ ID NO:4) is changed to Gln, and Lys-His-Arg-Arg (SEQ ID NO:1) 296–299 of human wild-type tPA (SEQ ID NO:4) is changed to Ala-Ala-Ala-Ala (SEQ ID NO:2) (TNK-tPA).

5. The process of claim 1 wherein the sample comprises human wild-type tPA (SEQ ID NO:4) and a variant thereof.

6. The process of claim 5 wherein the tPA variant is a tPA molecule wherein Thr103 of human wild-type tPA (SEQ ID NO:4) is changed to Asn, Asn117 of human wild-type tPA (SEQ ID NO:4) is changed to Gln, and Lys-His-Arg-Arg (SEQ ID NO:1) 296–299 of human wild-type tPA (SEQ ID NO:4) is changed to Ala-Ala-Ala-Ala (SEQ ID NO:2) (TNK-tPA).

* * * * *

UNITED STATES PATENT AND TRADEMARK OFFICE
CERTIFICATE OF CORRECTION

PATENT NO. : 6,828,118 B2
DATED : December 7, 2004
INVENTOR(S) : Yuan Xu It is certified that error appears in the above-identified patent and that said Letters Patent is hereby corrected as shown below:

Column 22,
Line 29, delete "Gin" and insert -- Gln --.

Signed and Sealed this

Twenty-sixth Day of April, 2005

JON W. DUDAS
*Director of the United States Patent and Trademark Office*